(12) United States Patent
Naka et al.

(10) Patent No.: US 7,295,307 B2
(45) Date of Patent: Nov. 13, 2007

(54) METHOD OF AND APPARATUS FOR MEASURING STRESS OF SEMICONDUCTOR MATERIAL

(75) Inventors: Nobuyuki Naka, Kyoto (JP); Akihiro Katanishi, Kyoto (JP); Masaaki Magari, Kyoto (JP)

(73) Assignee: Horiba, Ltd., Kyoto (JP)

( * ) Notice: Subject to any disclaimer, the term of this patent is extended or adjusted under 35 U.S.C. 154(b) by 196 days.

(21) Appl. No.: 11/219,550

(22) Filed: Sep. 2, 2005

(65) Prior Publication Data

US 2006/0049480 A1   Mar. 9, 2006

(30) Foreign Application Priority Data

Sep. 3, 2004   (JP) .............................. 2004-256929

(51) Int. Cl.
*G01J 3/44* (2006.01)
(52) U.S. Cl. ......................................... 356/301; 356/32
(58) Field of Classification Search ................ 356/301, 356/32
See application file for complete search history.

(56) References Cited

U.S. PATENT DOCUMENTS

| | | | |
|---|---|---|---|
| 4,812,036 A | | 3/1989 | Inoue |
| 5,864,393 A | * | 1/1999 | Maris .......................... 356/28 |
| 5,999,255 A | * | 12/1999 | Dupee et al. ............... 356/301 |

FOREIGN PATENT DOCUMENTS

| | | |
|---|---|---|
| GB | 2 241 606 | 9/1991 |
| JP | 64-32155 * | 2/1989 |
| JP | 3220433 | 9/1999 |

OTHER PUBLICATIONS

Hart, et al. "Temperature Dependence of Raman Scattering in Silicon", Jan. 15, 1970, Physical Review B, vol. 1, No. 2, pp. 638-642.*

* cited by examiner

*Primary Examiner*—Gregory J. Toatley, Jr.
*Assistant Examiner*—Kara E Geisel (57) ABSTRACT

The present invention provides a method of and a device for measuring the stress in a semiconductor material. An excitation light is irradiated on a semiconductor material formed with a silicon germanium layer and a strained silicon layer in a multilayer structure on a single crystal silicon substrate from the direction of the strained silicon layer. An internal stress of the semiconductor material is measured from peak position information of the Raman spectrum of scattered light from the irradiating point, wherein light having a wavelength capable of reaching the single crystal silicon substrate is used as the excitation light, a temperature of the semiconductor material is estimated from a shift amount of the peak position of the Raman spectrum of the scattered light from the substrate in accordance with the irradiation of the excitation light and the shift amounts of the peak positions of the Raman spectra in the strained silicon layer and in the silicon germanium layer are corrected by means of the estimated temperature, The internal stresses of the strained silicon layer and the silicon germanium layer are calculated from the corrected peak position information of the Raman spectra in the respective layers.

20 Claims, 10 Drawing Sheets

| Unit | Maker | Composition unit | Model | Specification |
|---|---|---|---|---|
| Raman | HORIBA Jobin Yvon | | LabRAM series | 300 (Focal lenth of spectrgraph : 300mm) |
| | | | | HR-800(Focal length of spectrograph : 800mm) |
| | | | | ARAMIS (Automation system) |
| | | | | IR (with FT-IR) |
| | | | U-1000 | Double monochromator |
| | | | T64000 | Triple monochromator |
| Typical laser of excitation line for Raman | Coherent (USA) | Laser head | INNOVA I-Line | Water cooled Ar laser, 363.8nm, 50mW |
| | | Power supply | | 208V, 60A |
| | | Heat Exchanger | | |
| | KIMMON Electric Co., Ltd. (Japan) | Laser head | IK3201R-F | He-Cd laser, 325.0nm, 20mW |
| | | Power supply | KR1801C | 100V, 10A |
| | Melles Griot (USA) | Laser head | 543-AP-A01 | Air cooled Ar laser, Tunable(457nm, 488nm, 514nm) |
| | | Power supply | 175B-200B | 200V, 30A |
| | | Remote fan | 6029 | - |
| | | Remote controller | IRC-003 | |
| | JDS Uniphase (USA) | Laser head | 2218-030SLS | Air cooled Ar laser, 488nm, 30mW |
| | | Power supply | 2110U-SLS | 100V, 20A |
| | | Remote fan | 152CFM 115V STANDARD | - |
| | | Remote controller | Remote interface controller | |
| Ellipsometer | HORIBA Jobin Yvon | | PZ2000-LE | Laser ellipsometer |
| | | | UVISEL | Spectroscopic ellipsometer |
| | | | MM-16 | Spectroscopic ellipsometer |
| X-Y stage | Nano Control Co., Ltd. (Japan) | X-Y stage | - | Stepping motor and piezo drive |
| | | Controller | | Special design for 12 inch wafer |
| Wafer table | - | Ceramics table and unit | Special model(for only HOR) | 6, 8, 12 inch wafer |
| | | Aluminum table and unit | Special model(for only HOR) | 6, 8, 12 inch wafer |
| Vibration isolator | Tokkyokiki Corporation (Japan) | Rigid base plate | alpha 4G-201M-1814-HS1 | Air spring / Active isolation |
| | | Active isolation unit | | |
| | | Isolation frame | | |
| Wafer transport equipment | HIRATA Corporation (Japan) | Robot | AR-WL180CL4-T-300-M | 8, 12 inch wafer (Double arm) |
| | | Aligner | KWA-12 | 8, 12 inch wafer |
| | | Foup opener | KWF-12B-8M | 12inch Foup and 8inch Open cassette |
| | | Body | - | - |

Fig. 9

| Unit | Maker | Composition unit | Model | Specification |
|---|---|---|---|---|
| Pattern Recognition system | SONY | CCD camera | XC-ES30 | 1/3 type IT CCD, EIA |
| | COGNEX | Video Capture Board | VPM-8100X-0000 | |
| Other units and parts | HORIBA | Fame<br>PC<br>FFU<br>Power supply<br>etc. | | |

METHOD OF AND APPARATUS FOR MEASURING STRESS OF SEMICONDUCTOR MATERIAL

BACKGROUND OF THE INVENTION

1. Field of the Invention

The present invention relates to a method of and a apparatus for measuring stress in a semiconductor material and for automatically measuring internal stresses of a thin film formed on a surface of a semiconductor substrate such as a silicon wafer or the like and fine processing parts variously patternized, which is incorporated into a manufacturing line of a semiconductor device or the like as a method of inspecting a product and a product material.

2. Description of Related Art

In a semiconductor device manufacturing process, quality control through the measurement of stresses of a thin film formed on a surface of a semiconductor substrate such as a silicon wafer or the like and fine processing parts of different patterns, a film thickness, a composition and the like is an significantly important and indispensable element for maintaining a stable performance of the manufactured semiconductor device.

In particular, in the semiconductor device, a complementary CMOS circuit is used in order to realize a high-performance large scale integrated circuit (LSI) in a sub 100 nm region, and it is very important to realize a higher speed in the CMOS circuit. As a technology for realizing the high-speed CMOS circuit has been developed a manufacturing technology for the semiconductor device in which strained silicon having a carrier motility larger than that of a conventional silicon is used. The technology is aimed at improving the carrier mobility in such manner that a silicon layer is formed on a silicon germanium layer (including SiGe layer recited below) having a large grating constant, and a tensile strain is applied to the silicon layer (thin film) so as to modulate a silicon band structure.

In the technology of the strained silicon, the quality control, which includes the measurement of the internal stress of the SiGe layer, let alone the measurement of a stress state of the strained silicon layer, and preferably, the control of the film thickness of each layer, the measurement of a germanium (Ge) content in the SiGe layer and the like, plays a very important role in improving the productivity of the high-performance and high-speed semiconductor device.

In general, Raman spectroscopic technology is adopted for measuring the stress of the semiconductor material such as silicon. To describe the stress measurement using the Raman spectroscopic technology, it is generally known that, for example, a peak position of the Raman spectrum is shifted by approximately 1 cm when the stress of 0.5 φ Pa acts on a single crystal silicon, and the shift of the peak position of the Raman spectrum is utilized to estimate a stress at a measurement point based on the change of the peak position of the Raman spectrum.

In order to apply the stress measurement by the Raman spectroscopy to the foregoing strained silicon to thereby obtain a highly accurate measurement result and measurement reproducibility for maintaining the highly accurate measurement result in a stable manner for a long period of time, it is vital to constantly control a shift amount of the peak position of the Raman spectrum to approximately 0.01 cm. However, the shift of the peak position of the Raman spectrum in accordance with variations generated in an optical system by changing ambient temperature, examples of which are a wavelength shift caused by a minor strain of any optical component and a temperature change of the semiconductor material itself as a measuring object (for example, in the case of the single crystal silicon, the peak position shifts by approximately 0.02 cm when the temperature changes by 1° C.), is inevitable. Therefore, when the generally available Raman spectroscopic technology is directly applied to the measurement of the stress of the strained silicon, it becomes very difficult to assure a predetermined measurement accuracy and measurement reproducibility.

In order to deal with the problems mentioned above in measuring the stress of the strained silicon using the generally available Raman spectroscopy, a conventional method, in which a plasma line of a gas laser is fetched along with the Raman light (scattered light generated by the irradiation of an excitation light) and a shift amount of a peak position of the plasma line is used to correct the peak position of the Raman spectrum so that the stress is measured based on the corrected peak position of the Raman spectrum, was proposed (for example, see No. 2001-66197 of the Publication of an Unexamined Japanese Patent Application).

Further, as a technology for measuring the internal stress of a material such as semiconductor using Raman spectroscopy, a stress evaluation method, in which a temperature of a material to be measured at a measurement point is changed, a plurality of peak wave numbers of the Raman spectrum variable in response to the temperature change are measured, and the plurality of measurement values (peak wave number) are subjected to a statistical processing at each measurement point so that data free of any influence from the temperature change of the measured material itself at the measurement point can be obtained, was proposed (for example, see No. H06-82098 of the Publication of the Unexamined Japanese Patent Application).

Figure 3:
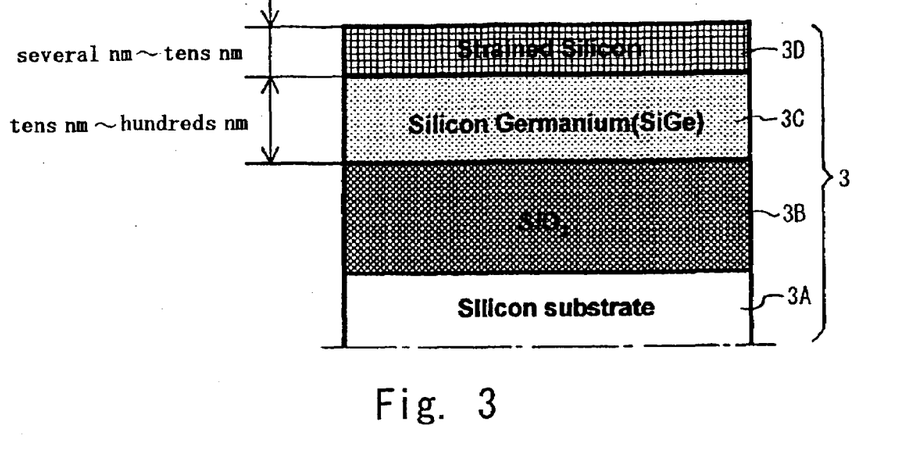
FIG. 3 is a sectional view illustrating a structure of a semiconductor material using strained silicon as a measuring object.

As shown in FIG. 3, a semiconductor material 3 using strained silicon as a typical measuring object is formed from, for example, serially providing a SiGe layer 3C of several 10 nm-several 100 nm and a strained silicon layer 3D of several nm-several 10 nm in a multilayer structure on a single crystal silicon substrate 3A via a silicon oxide layer (hereinafter referred to as SiO2 layer) 3B. The semiconductor material 3 having the multilayer structure is constituted in such manner that the stress does not act on the substrate 3A itself in the presence of the SiO2 layer 3B between the single crystal silicon substrate 3A and the SiGe layer 3C. Therefore, the Raman spectrum of the substrate 3A at the time of irradiating an excitation light from the direction of the strained silicon layer 3D is in a non-stress state, which can lead to the conclusion that the shift, if any, generated in the peak position of the Raman spectrum of the substrate 3A results from the influence of the temperature change of the measured semiconductor material 3 itself.

Figure 6:
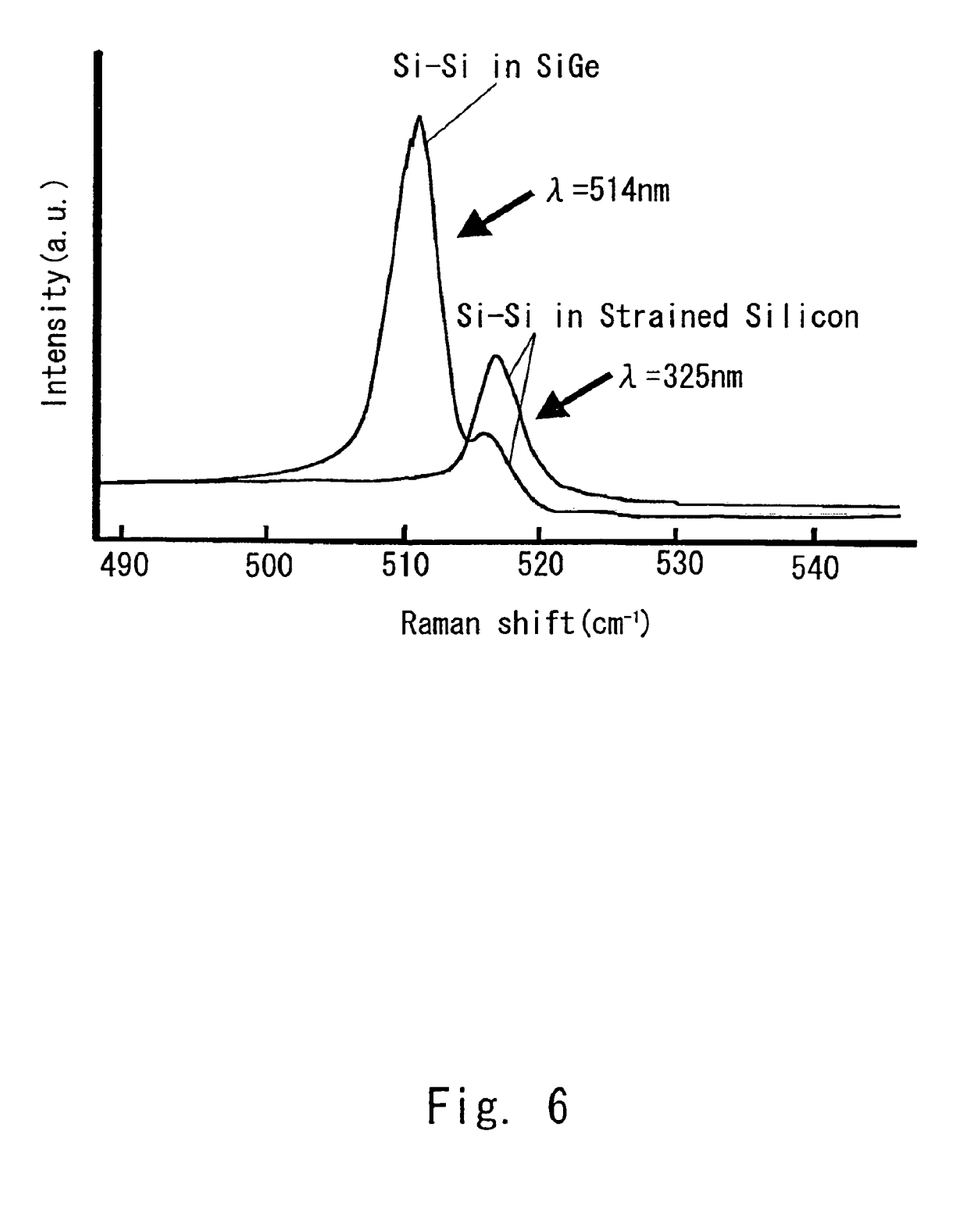
FIG. 6 is a diagram illustrating a relationship between a wavelength and a spectral intensity of Raman spectrum in each layer obtained when an excitation light generated by a laser source of a wavelength having a large penetration depth is irradiated on the semiconductor material using the strained silicon.

Further, it is important to select a wavelength of the excitation light, on which a penetration depth of a light largely depends, in measuring the Raman spectrum of the semiconductor material 3 using the strained silicon. Of Ar lasers typically used for the Raman spectroscopy, an Ar ion laser having the wavelength (λ) of 514,488,457 nm, which is an oscillation beam having a relatively large intensity, penetrates at the depth of 760,560,310 nm, and an He—Cd laser having the wavelength (λ) of 325 nm penetrates at the depth of approximately 10 nm. Therefore, in the case of measuring the Raman spectrum using the excitation light generated by the Ar ion laser having the wavelength of 514 nm and large penetration depth, as shown in FIG. 6, the Raman spectrum having a large intensity can be detected due to a Si—Si band (peak wavelength) in the SiGe layer 3C, while the Raman spectrum of the Si—Si band in the strained silicon layer 3D cannot be detected under the influence of the Raman spectrum of the substrate 3A. Therefore, it is necessary to use a ultraviolet light such as an He—Cd ion laser having the wavelength of 325 nm in order to unfailingly detect only the Raman spectrum of the strained silicon layer 3D which is the uppermost layer.

On the other hand, when the laser having a small wavelength and a small penetration depth is used, the excitation light does not reach the SiGe layer 3C, which makes it impossible to measure the Raman spectrum of the SiGe layer 3C. Therefore, it becomes necessary to use a visible light having a long wavelength as the excitation light in order to measure the Raman spectrum of the SiGe layer 3C or the substrate 3A.

While it is possible to avoid any influence from the changing ambient temperature by controlling the variations of the optical system caused by the change of the ambient temperature by means of the conventional method recited in No. 2001-66197 of the Publication of the Unexamined Japanese Patent Application in the case of measuring the Raman spectrum of the strained silicon layer 3D using the ultraviolet light as the excitation light, the influence received from the temperature change of the measured semiconductor material itself easily results in the generation of a large error in a predetermined stress measurement. Therefore, in the pursuit of assuring a highly accurate measurement undergoing fewer errors and stable measurement reproducibility in a long period of time, a temperature adjusting mechanism for maintaining the temperature of the semiconductor material at a constant degree or the like and a number of additional steps are unfavorably required in order to avoid any influence from the temperature change of the measured material itself. The additional steps are, for example, a specimen for correcting the temperature is prepared apart from the semiconductor material to be measured and a spectrum of the correction specimen is measured prior to the measurement of the semiconductor material so that the peak position of the Raman spectrum influenced by the temperature change of the semiconductor material is corrected based on the measurement information and the predetermined stress measurement can be thereby implemented.

In the case of the conventional method recited in No. H06-82098 of the Publication of the Unexamined Japanese Patent Application, a large number of steps and a resultant large amount of time are required for measuring the stress of even one material to be measured in order to obtain a highly accurate measurement result eliminating any influence from the temperature change of the measured material itself. The required steps are, for example, the temperature is changed at each of the plurality of measurement points, the plurality of peak wave numbers of the Raman spectrum variable in response to the temperature change are measured, and the plurality of measurement values (peak wave number) are subjected to statistical processing at each measurement point. As a result, a remarkable deterioration of a productivity is triggered by incorporating the measurement of the stress of the semiconductor material having the foregoing disadvantages into the manufacturing line in which a high speed and continuity are demanded, such as the manufacturing of the semiconductor device. Thus, it is practically not possible to introduce such a stress measurement. In addition, the conventional method serves to correct the change of the peak wave number of the Raman spectrum due to a temperature difference resulting from the different configurations of the respective components when the excitation light is irradiated on a single material as a measuring object and does not respond to the influence from the temperature change of the entire material to be measured. As described, the conventional method included such problems that the measurement accuracy was inevitably lowered due to the shift of the peak position of the Raman spectrum in accordance with the temperature change of the measured material itself and the measurement reproducibility could not be assured in a long term.

The present invention was implemented in order to solve the foregoing problems, and a main object is to provide a method of and an apparatus for measuring the stress of the semiconductor material requiring neither the temperature adjusting mechanism for maintaining the temperature of the semiconductor material at a constant degree nor any additional step and capable of performing the predetermined stress measurement with a high accuracy and at a high speed irrespective of the changing ambient temperature and the temperature change of the material itself.

SUMMARY OF THE INVENTION

In order to achieve the foregoing object, a method of measuring a stress of a semiconductor material of the present invention is a method of measuring a stress in a semiconductor material wherein an excitation light is irradiated on a semiconductor material formed from providing a silicon germanium layer and a strained silicon layer in a multilayer structure on a single crystal silicon substrate from the direction of the strained silicon layer. An internal stress of the semiconductor material is measured from peak position information of the Raman spectrum of a scattered light from the irradiating point, characterized in that a light having a wavelength capable of reaching the single crystal silicon substrate is used as the excitation light, a temperature of the semiconductor material is estimated from a shift amount of the peak position of the Raman spectrum of the scattered light from the substrate in accordance with the irradiation of the excitation light of the foregoing wavelength. The shift amounts of the peak positions of the Raman spectra in the strained silicon layer and in the silicon germanium layer are corrected by means of an estimated temperature, and the internal stresses of the strained silicon layer and the silicon germanium layer are calculated from the corrected peak position information of the Raman spectra in the respective layers.

An apparatus for measuring a stress of a semiconductor material of the present invention includes an apparatus for measuring stress of a semiconductor material wherein an excitation light is irradiated on a semiconductor material formed from providing a silicon germanium layer and a strained silicon layer in a multilayer structure on a single crystal silicon substrate from the direction of the strained silicon layer. An internal stress of the semiconductor material is measured from peak position information of the Raman spectrum of a scattered light from the irradiating point, characterized in comprising a laser source for generating the excitation light having a wavelength capable of reaching the single crystal silicon substrate, a Raman spectroscopic optical system for irradiating the excitation light on the semiconductor material from the strained-silicon-layer side to the single crystal silicon substrate and outputting peak position shift information of the Raman spectrum of the scattered light from the substrate on which the excitation light is irradiated. An operating unit estimates a temperature of the semiconductor material from the peak position shift information of the Raman spectrum, and corrects the peak position shift amounts of the Raman spectra in the strained silicon layer and in the silicon germanium layer by using the estimated temperature calculations of the internal stresses of the strained silicon layer and the silicon germanium layer from the corrected peak position information of the Raman spectra in the respective layers is then performed.

In a method of measuring the stress of the semiconductor material, it is preferable that at least one of the shift amount of the peak position, spectral full width at half maximum, spectral intensity and spectral area of the Raman spectrum in each of the single crystal silicon substrate, strained silicon layer and silicon germanium layer constituting the semiconductor material be used as parameters to calculate film thicknesses of the strained silicon layer and the silicon germanium layer and/or a germanium content in the silicon germanium layer at the same time as the calculation of the internal stresses.

In an apparatus for measuring the stress of the semiconductor material, the operating unit is preferably provided with a means for calculating the film thicknesses of the strained silicon layer and the silicon germanium layer and/or the germanium content in the silicon germanium layer at the same time as the calculation of the internal stresses using at least one of the shift amount of the peak position, spectral full width at half maximum, spectral intensity and spectral area of the Raman spectrum in each of the single crystal silicon substrate, strained silicon layer and silicon germanium layer constituting the semiconductor material as parameters.

Further, in an apparatus for measuring the stress of the semiconductor material, the Raman spectroscopic optical system is preferably provided with a plurality of laser sources having different wavelengths and a laser beam selecting unit for selectively switching laser beams irradiated from the plurality of laser sources.

A current temperature of the measured semiconductor material is estimated from the peak position shift amount of the Raman spectrum in the non-stress state from the substrate obtained by irradiating the excitation light so as to reach the single crystal silicon substrate, and the peak position shift amounts of the Raman spectrum in the strained silicon layer and in the silicon germanium layer (SiGe layer) stacked on one another on the substrate are corrected so that the stresses of the strained silicon layer and the SiGe layer can be accurately measured irrespective of, for example, any variations in the optical system such as a wavelength shift due to any strained optical component and a deteriorated optical filter resulting from changing ambient temperature, which causes the peak position shift of the Raman spectrum, influenced by the temperature of the measured semiconductor material itself, and the like. Therefore, it becomes unnecessary to provide a temperature adjusting mechanism for maintaining the temperature of the semiconductor material itself at a constant degree and the additional steps such as measuring the Raman spectrum of the specimen for correcting the temperature, which is prepared apart from the semiconductor material, prior to the measurement of the semiconductor material as the measuring object so as to correct the peak position of the Raman spectrum influenced by the temperature change of the semiconductor material based on the measurement information. As a result, stress can be measured with a high degree of accuracy, at a high speed and at a low cost free from any influence from temperature. Further, such a highly accurate and high-speed stress measurement can be reproduced in a stable manner for a long period of time. Thereby, as a result of such an effect, the productivity of a semiconductor device provided with the semiconductor material using the strained silicon can be greatly improved.

Further, as described, not only the predetermined stress calculation but also the calculation of the respective physical quantities such as the film thicknesses of the strained silicon layer and SiGe layer and/or the Ge content in the SiGe layer and the like can be implemented using the shift amount of the peak position, spectral full width at half maximum, spectral intensity, spectral area and the like in each of the layers constituting the semiconductor material as parameters. Thereby, quality control in the semiconductor material can achieve a higher performance so that the quality of the manufactured semiconductor device can be further improved, and the inspecting steps and facility can be simplified possibly leading to productivity improvement and the reduction of the manufacturing cost.

Further, a plurality of laser sources having different wavelengths are provided in the Raman spectroscopic system, and any of the laser beams having the different wavelengths from the laser sources can be selectively irradiated on the semiconductor material. Accordingly, the excitation light can unfailingly reach the substrate irrespective of what general thickness and thickness ratios of the respective layers the measured semiconductor material has. Then, the temperature of the semiconductor material can be accurately estimated based on the peak position shift amount of the Raman spectrum from the substrate and the peak position shift amounts of the Raman spectra in the strained silicon layer and the SiGe layer can be accurately corrected based on the estimated temperature. As a result, a predetermined stress measurement achieving a high accuracy and a high speed can be reliably and stably implemented.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 8 is an equipment table for the first embodiment; and

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Hereinafter, preferred embodiments of the present invention are described referring to the drawings.

Figure 1A:
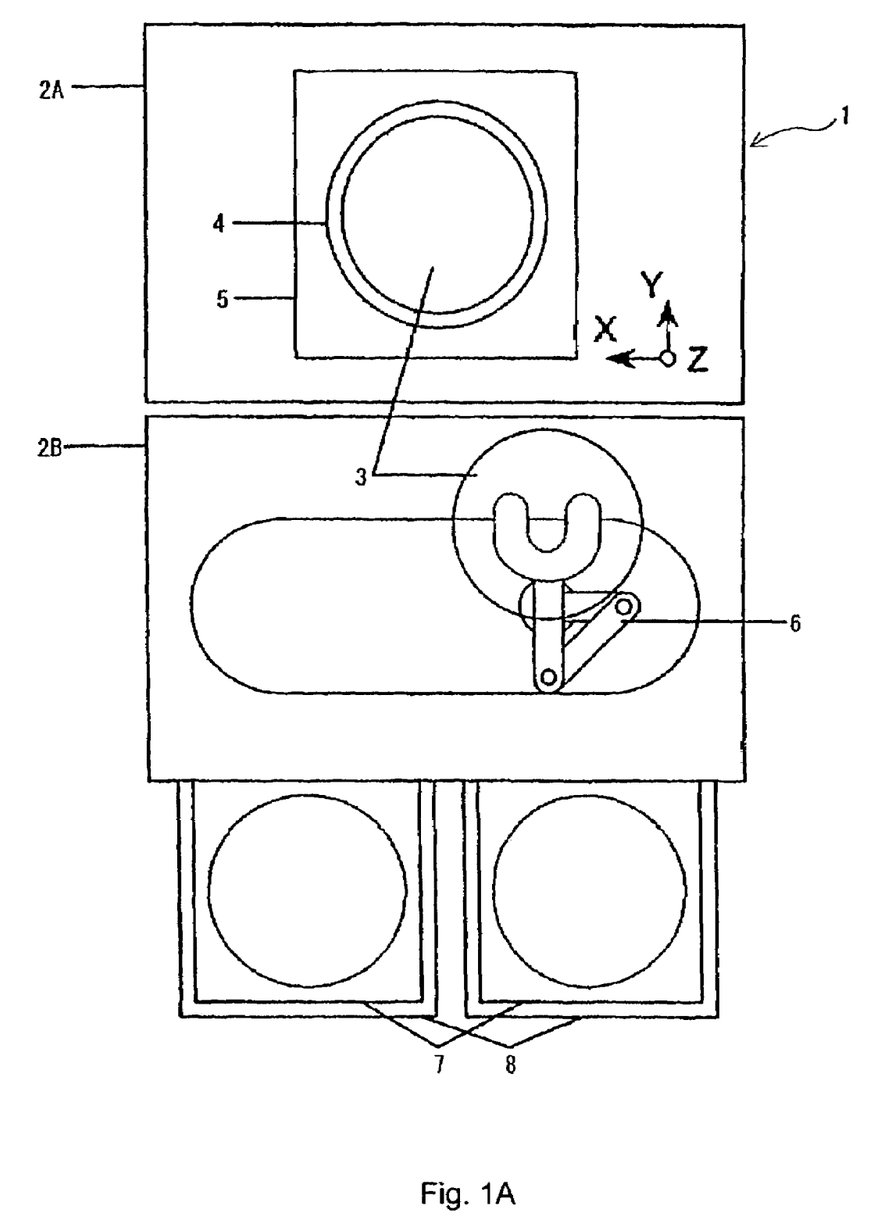
FIG. 1A is a plan view schematically showing an entire configuration of a substrate examining device according to a first embodiment of the present invention.
Figure 1B:
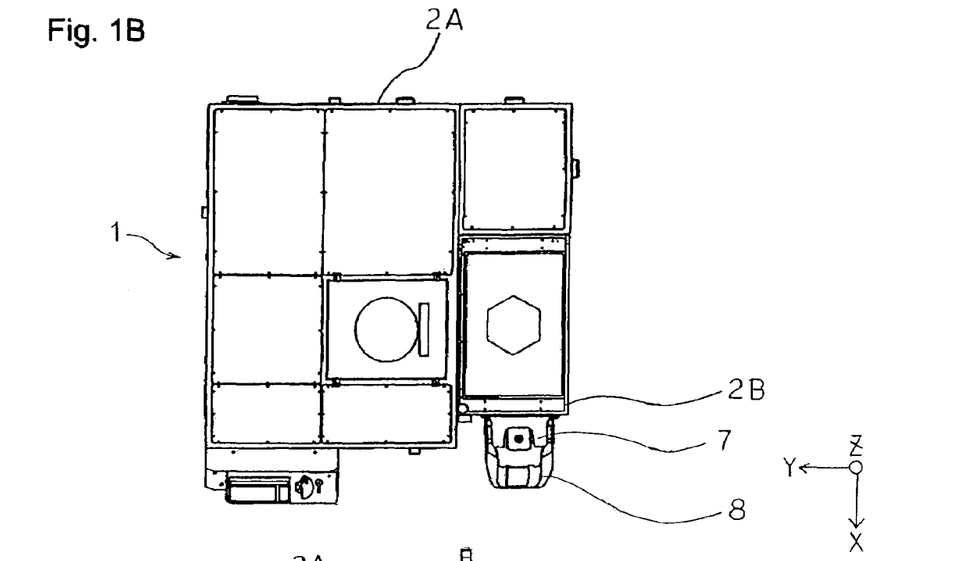
FIG. 1B is a plan view of a substrate examining device.
Figure 1C:
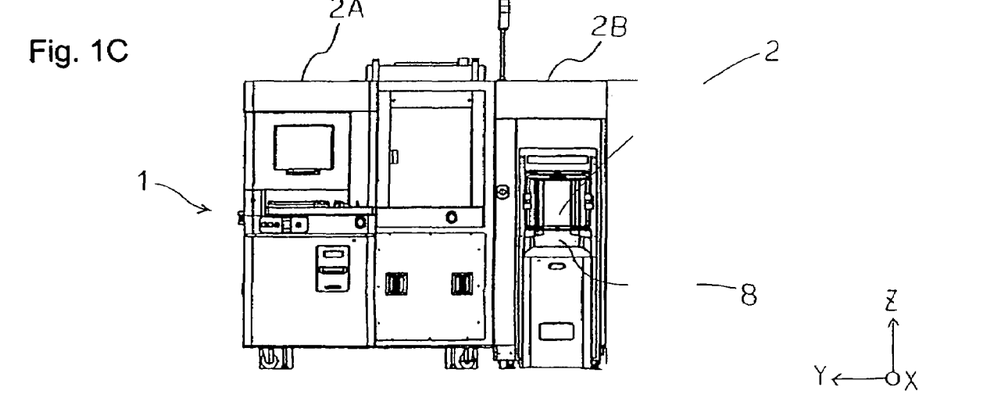
FIG. 1C is a front elevational view of a substrate examining device.
Figure 1D:
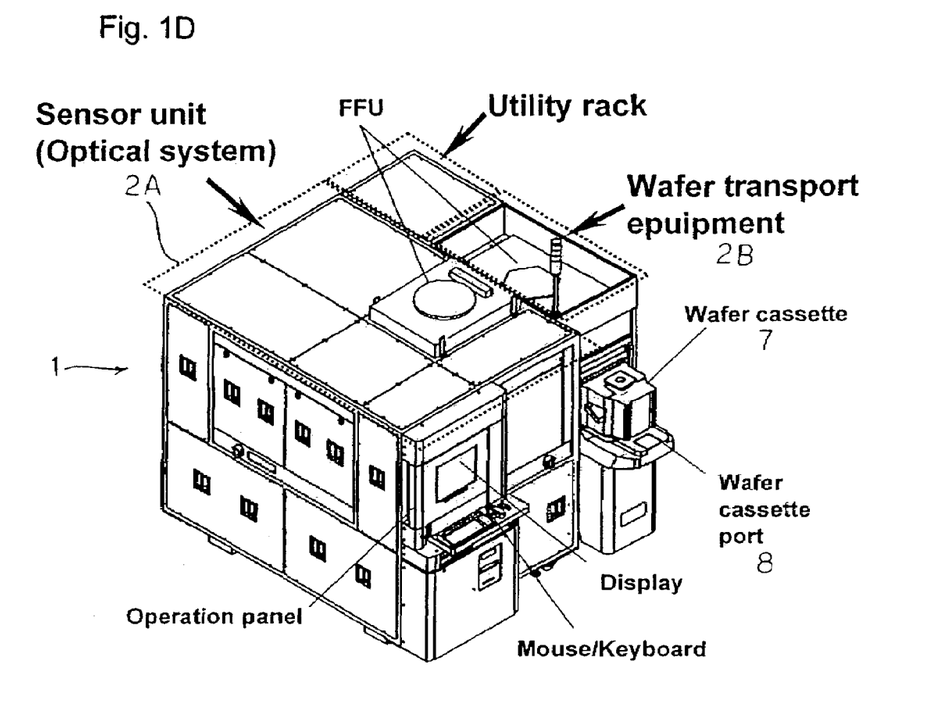
FIG. 1D is a front perspective view of a substrate examining device.
Figure 1E:
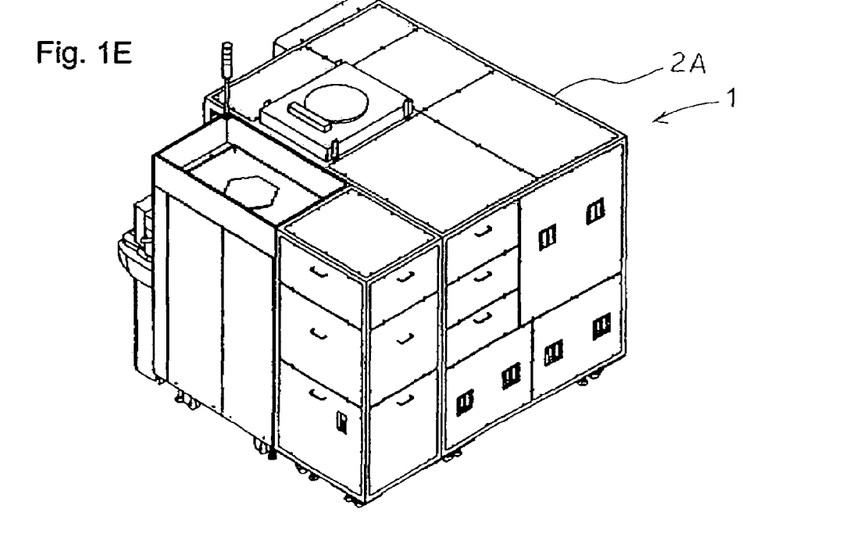
FIG. 1E is, a rear perspective view of a substrate examining device.
Figure 2:
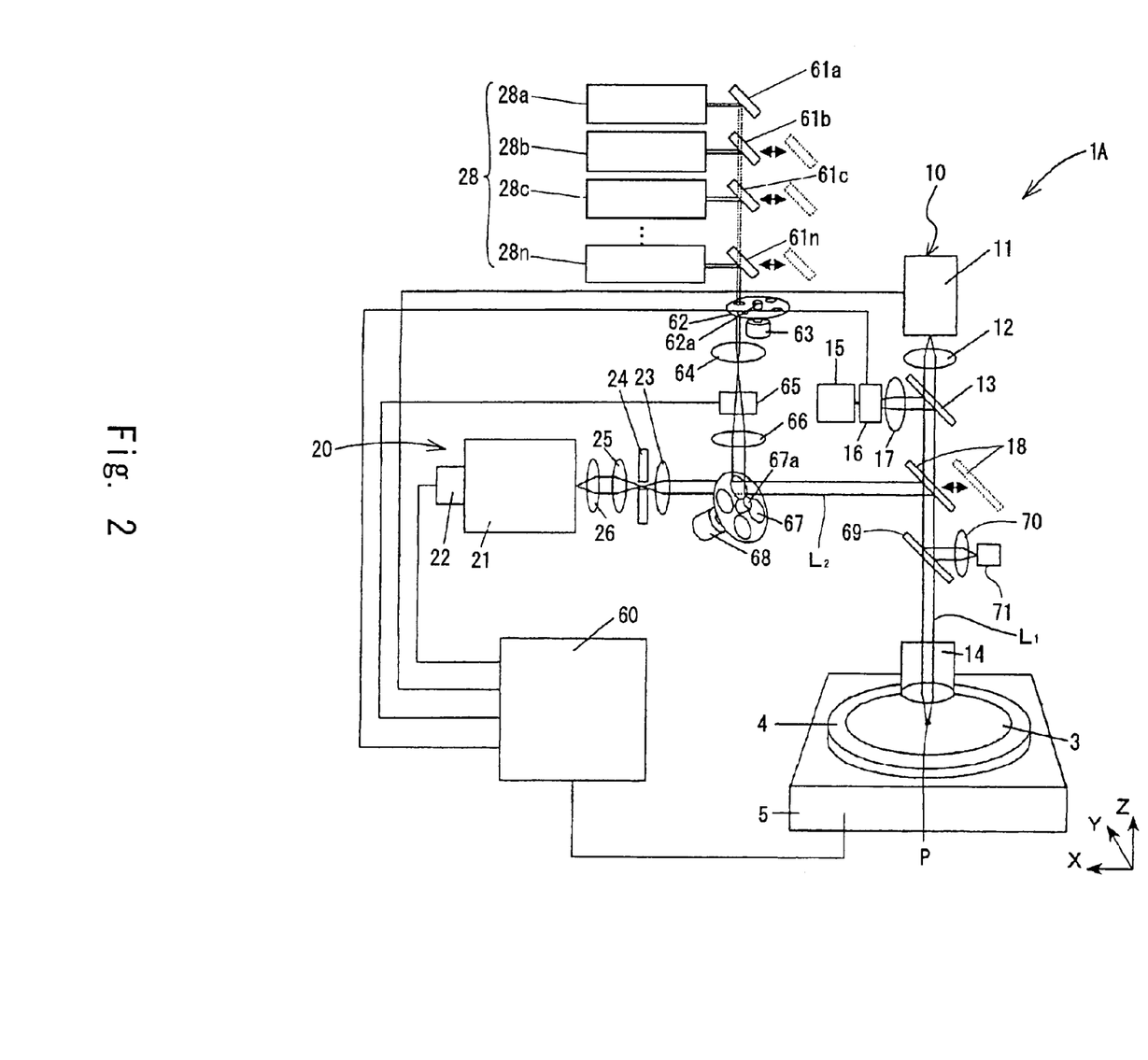
FIG. 2 is a view illustrating a constitution of a stress measuring system as a main part of the substrate inspection apparatus according to the first embodiment.

FIG. 1A is a plan view schematically showing an entire configuration of a substrate inspection apparatus 1 according to a first embodiment of the present invention and FIG. 2 is a view showing a configuration of a stress measuring system as a main part of the substrate inspection apparatus 1. In FIG. 1A, 2A is a measuring chamber of the substrate inspection apparatus 1 equipped with a Raman spectroscopic optical system/ellipsometric optical system, 2B is a transport equipment set up next to the measuring chamber 2A, 3 is a substrate (sample, hereinafter referred to as a wafer) of for example, a silicon wafer formed by applying the strained silicon technique where the thin film of silicon layer is formed on the SiGe layer with large lattice constant, 4 is a sample stage configured so as to be movable in a three-dimensional direction of horizontal direction (X, Y directions) and height direction (Z direction), and 5 is a driving section of the sample stage 4.

In FIG. 1A, 6 is a robot arm with a function of grasping the wafer 3 and transporting the same onto the sample stage 4, 7 is a case for accommodating a plurality of wafers 3 so as to be stacked in a longitudinal direction with a predetermined spacing, and 8 is a case table or stand for mounting the case 7. The wafer 3 accommodated so as to be stacked in the longitudinal direction, for example, is taken out one by one and transported to the sample stage 4 and the examined wafer 3 is again returned to the original location by means of the robot arm 6. However, when arranging two cases 7 next to each other as in the first embodiment, the wafer 3 taken out from one case 7 and examined may be accommodated in the other case 7 one by one.

FIGS. 1B, 1C, 1D and 1E are views illustrating a substrate inspection apparatus 1 according to a first embodiment for implementing a method of measuring stress of a semiconductor material according to the present invention. As can be determined, modular components can be mounted to form the overall substrate inspection apparatus. FIG. 2 is a view illustrating a stress measuring system 1A as a main part of the substrate inspection apparatus 1. Referring to the reference symbols shown FIGS. 1B through 1E and FIG. 2, 2A denotes a measurement chamber or sensor unit of the stress measuring system 1A in which a Raman spectroscopic optical system is installed, 2B denotes a wafer transport unit disposed adjacent to the measurement chamber 2A, 3 denotes a semiconductor material as a measuring object (hereinafter, simply referred to as wafer), 4 denotes a specimen table, and 5 denotes a drive section for moving the specimen table 4 in a three-dimensional direction including a horizontal direction (X and Y directions) and a vertical direction (Z direction).

The robot arm 6 in the wafer transport equipment 2B can have a function of grasping the wafer 3 and transporting it onto the specimen table 4, 7 denotes cases in which a plurality of wafers 3 are vertically stacked on one another with predetermined intervals there between, and 8 denotes case tables on which the cases 7 are disposed. For example, the wafers 3 housed in the vertical multilayer structure can be serially retrieved one by one and transported onto the specimen table 4, and the post-measurement wafer 3 can be returned to the original position by means of the robot arm. However, in the case of disposing the two cases 7 adjacent to each other as in the first embodiment, the wafers 3 retrieved from one of the cases 7 can be serially housed in the other case 7 after the inspection.

The wafer 3 as a measuring object is, for example, formed from a multilayer structure in which a SiGe layer 3C of several 10 nm-several 100 nm and a strained silicon layer 3D of several nm—several 10 nm are serially stacked on one another on a single crystal silicon substrate 3A via a silicon oxide layer (hereinafter, referred to as $SiO_2$ layer) 3B as described referring to FIG. 3.

Figure 1F:
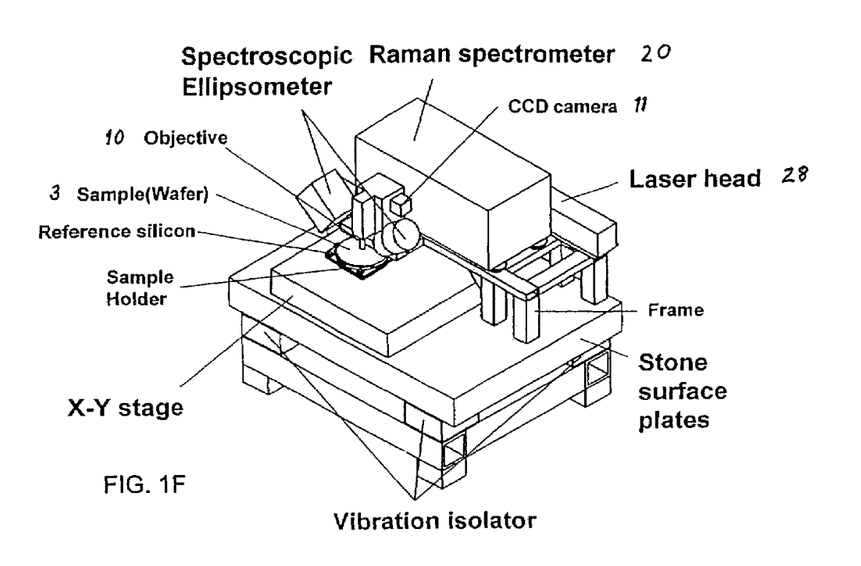
FIG. 1F is a front perspective view of components in a sensor unit.

In FIG. 2 and FIG. 1F, a reference numeral 10 denotes an optical microscope for observing a surface of the wafer 3. The optical microscope 10 comprises a CCD camera 11 disposed on an optical axis $L_1$ substantially perpendicular to the surface of the wafer 3, a condensing lens 12 disposed on the optical axis $L_1$, a beam splitter (half mirror) 13, an objective lens 14, a white light source 15 for irradiating a white light on the wafer 3 via the half mirror 13, a shutter 16 and a collimator lens 17. A reference numeral 18 is a movable mirror provided on the optical axis $L_1$. The stress measuring system 1A is adapted to observe a measurement point P in a minute region on the surface of the wafer 3 by means of the optical microscope 10 when the mirror 18 is moved to a position shown in a phantom line in FIG. 2. The white light source 15, shutter 16 and collimator lens 17 are provided on an optical axis orthogonal to the optical axis $L_1$.

A reference numeral 20 denotes a sensor unit such as a Raman spectroscopic optical system for detecting the Raman light by irradiating a laser beam on the wafer 3 based on the optical axis $L_1$ in the same manner as in the optical microscope 10 when the mirror 18 is moved to a position shown in a solid line in FIG. 2. The Raman spectroscopic optical system 20 comprises a spectrograph 21 disposed on an optical axis $L_2$ from which the light is reflected in a direction orthogonal to the optical axis $L_1$ by the mirror 18, a detector 22 for detecting the spectrally split Raman light, a condensing lens 23 for adjusting the Raman light entering the spectrograph 21, a pinhole 24, a collimator lens 25, a condensing lens 26, a disk 62 rotated by a stepping motor 63 and provided with an optical filter (bandpass filter) 62a for cutting a light of any wavelength other than an excitation light emitted from a laser source selected from a plurality of laser sources 28a, 28b, 28c, . . . , 28n having different wavelengths $\lambda_1$-$\lambda_n$ and constituting a laser source 28, a condensing lens 64, a laser beam shutter 65 for intercepting the laser beam, a collimator lens 66 for converting the laser beam into a collimated beam and a disk 67 rotated by a stepping motor 68 and provided with an optical filter 67a for guiding the laser beam to the wafer 3 and thereafter cutting the Rayleigh light, wherein a laser beam selecting device capable of automatically selectively changing the laser beam irradiated on the measurement point P of the wafer 3 is provided.

Figure 7:
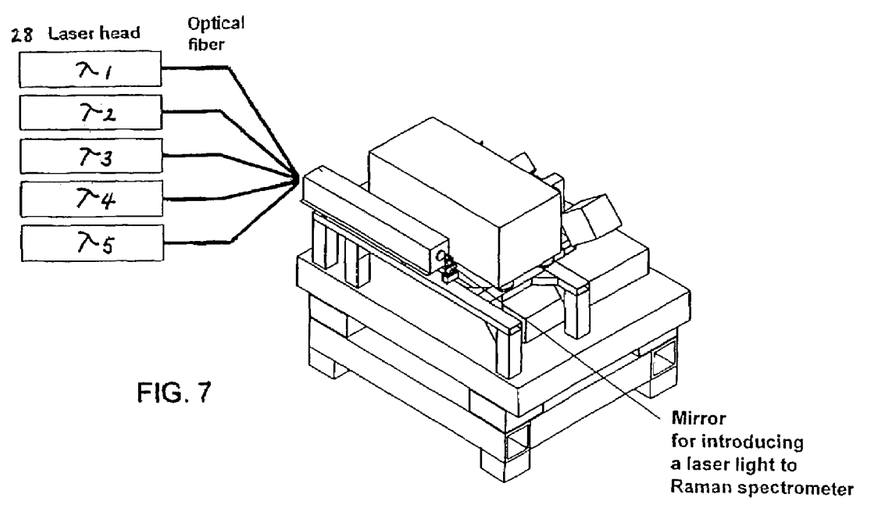
FIG. 7 is a back perspective view of components in a sensor unit with illustration of use of a plurality of laser heads of a different wavelength.

As shown in the rear perspective view of FIG. 7, the laser source or laser head 28 can have a plurality of laser sources of different wavelengths that can be connected by optical fibers or by a server of movable mirrors to introduce a specific wavelength of laser light $\lambda_a$ to the Raman spectrometer.

To be more specific about the plurality of laser sources 28a, 28b, 28c, . . . , 28n having the different wavelengths and constituting the laser source 28, Ar lasers 28a, 28b, 28c, . . . whose wavelengths are respectively set to 514 nm, 488 nm, 457 nm, 364 nm . . . , and a He—Cd ion laser 28n set to emit a ultraviolet light having the wavelength of 325 nm are used. At positions opposite to oscillation parts of the laser sources 28a, 28b, 28c, . . . , 28n are disposed movable mirrors for changeover of optical path 61a, 61b, 61c, . . . , 61n for selecting one of the laser beams having the different wavelengths and guiding the selected laser beam to the wafer 3 to be measured.

In the Raman spectroscopic analysis, the ultraviolet light having the wavelength of 325 nm may be used as the excitation light. Therefore, on the ground that a focal point may differ in an auto focus mechanism in which an image is obtained by the light made to enter the CCD camera 11 by the condensing lens 12, a detector 71 for detecting the focal point is provided so as to adjust the focal point position in such manner an intensity of the Rayleigh light is detected through a beam splitter 69 and a condensing lens 70 disposed on the optical axis $L_1$ in the same manner as in the optical microscope 10, and the drive section 5 of the specimen table 4 is controllably moved in the Z direction (vertical direction) so that the detected value of the Rayleigh light intensity results in a maximum value. As known, an appropriate vibration isolator can be provided.

A reference numeral 60 denotes an operating process device (hereinafter, referred to as computer) which is connected to the transport unit 2B, drive section 5 of the specimen table 4, optical microscope 10, Raman spectroscopic optical system 20, a drive section of the movable mirror 18 (not shown) and the like so as to generally control the substrate inspection apparatus 1. In the computer 60 are memorized, for example, a control program Pa instructing an inspecting sequence in which the transport unit 2B, drive section 5, optical microscope 10, Raman spectroscopic optical system 20 and the like are controlled so that the plurality of wafers 3 housed in the cases 7 are serially retrieved one by one and placed on the specimen table 4 to be thereby subjected to successive inspections and the inspected wafer 3 is housed in the case 7 again, an inspection result output program Pb instructing such actions as implementing the operating process to the inspection result and displaying it on a display screen or recording it on a medium, inspection recipe data D1 in which measurement conditions with respect to the respective wafers 3 and conditions for outputting the inspection result are recorded and Data D2 in which the inspection result is stored. An operation panel and input controls such as a mouse/keyboard can be provided for the operator.

FIG. 8 is an equipment table for the first embodiment.

By the way, the content of the inspection recipe or menu is shown as follows:

Recipe Content
(1) Setting of measurement conditions of Raman spectrophotometric system
(2) Diffraction grating
(3) Center of measurement range
(4) ND filter (adjustment of laser power)
(5) Hole diameter (confocal optical system)
(6) Entrance slit width (spectrograph)
(7) Measurement data integrated time
(8) Number of accumulated spectra
(9) Setting of presence or absence of auto-focus
(10) Range of curve fitting (plurality acceptable)
(11) Fitting curve function (Gauss/Lorentz/Gauss+Lorentz)
(12) Number of fitting curves
(13) Initial value of fitting curve [1] Peak shift, peak intensity, full width at half maximum
(14) Arithmetic expression Ex. Stress-strain value calculation calibration curve
(15) Output parameters Peak shift, peak intensity, full width at half maximum, stress, strain, etc.
2. Setting of measurement point coordinates
3. Setting of measurement conditions of calibration samples Content is same as that of Section 1. (1) through (15).
4. Setting of presence or absence of measurement of calibration samples Below is described the inspection sequence of the control program Pa. When a user disposes the cases 7 in which the plurality of wafers 3 are housed on the case tables 8 and activates the substrate inspection apparatus 1 as shown in FIG. 1, the robot arm 6 of the transport unit 2B retrieves one of the wafers 3 from the case 7 and places it on the specimen table 4 under the control of the computer 60.

Next, the wafer 3 is maintained in the horizontal state, and the drive section 5 is subjected to the control of the computer 60. Thereby, the position of the wafer 3 is moved in the Z direction (vertical direction) and X-Y direction (horizontal direction) so that the focal point position of the optical microscope 10 falls on the measurement point P which is one of a plurality of measurement points shown by measurement point data Da. Because of a possible shift vertically generated in the measurement point P if the wafer 3 is warped, the position of the wafer 3 is finally determined while the image created on the surface of the wafer 3 is observed by the optical microscope 10 or Raman spectroscopic optical system 20 and the drive section 5 is moved in the Z direction.

More specifically, in the case of determining the position in the Z direction by means of the optical microscope 10, the computer 60 closes the shutter 65 of the Raman spectroscopic optical system 20 and retreats the reflecting mirror 18 to the position shown in the phantom line, and, in the foregoing state, opens only the shutter 16 of the optical microscope 10. Then, the light from the white light source 15 is reflected by the half mirror 13 and irradiated on the surface of the wafer 3 via the objective lens 14. The light from the surface of the wafer 3 transmits through the objective lens 14 and the half mirror 13 and enters the CCD camera 11 via the condensing lens 12. As a result, the computer 60 can obtain the image at the focal point position of the objective lens 14. Then, the computer 60 appropriately moves the drive section 5 in the Z direction (vertical direction) so as to adjust the focal point position when the focal point of the image obtained by the optical microscope 10 is shifted.

In the case in which the wavelengths of the lights measured by the Raman spectroscopic optical system 20 and the optical microscope 10 are largely different, the focal point position can be corrected in such manner that the Rayleigh light intensity is detected through the beam splitter 69 and the condensing lens 70 disposed on the optical axis L1 in the same manner as in the optical microscope 10 and the drive section 5 of the specimen table 4 is controllably moved in the Z direction (vertical direction) so that the detected value of the Rayleigh light intensity results in the maximum value.

When the foregoing adjustment of the focal point position is completed, the computer 60 moves the reflecting mirror 18 to the position shown in the solid line and opens the shutter 65 of the Raman spectroscopic optical system 20 and thereby executes its control so that the laser beam from the laser source 28 can be reflected by the collimator lens 66, optical filter 67a of the disk 67 and reflecting mirror 18 and irradiated on the measurement point P on the surface of the wafer 3 via the objective lens 14.

In the foregoing case, of the plurality of laser sources 28a, 28b, 28c, . . . , 28n, the laser source having the wavelength enabling the excitation light to reach the single crystal silicon substrate 3A is selected in accordance with the thicknesses of the strained silicon layer 3D, SiGe layer 3C and $SiO_2$ layer 3B stacked on one another on the single crystal silicon substrate 3A in the wafer 3. When the excitation light of the selected wavelength is irradiated on the measurement point P of the wafer 3 via the optical filter 67a of the disk 67 rotated by the stepping motor 68, the light generated at the measurement point P on the surface of the wafer 3 is guided to the optical axis L2 by the objective lens 14 and the reflecting mirror 18, and the Raman scattered light excluding the Rayleigh light transmits through the optical filter 67a and enters the spectrograph 21 via the respective optical systems 23-26. Further, a spectral intensity of the Raman scattered light spectrally split by the spectrograph 21 is detected by the detector 22.

Figure 4:
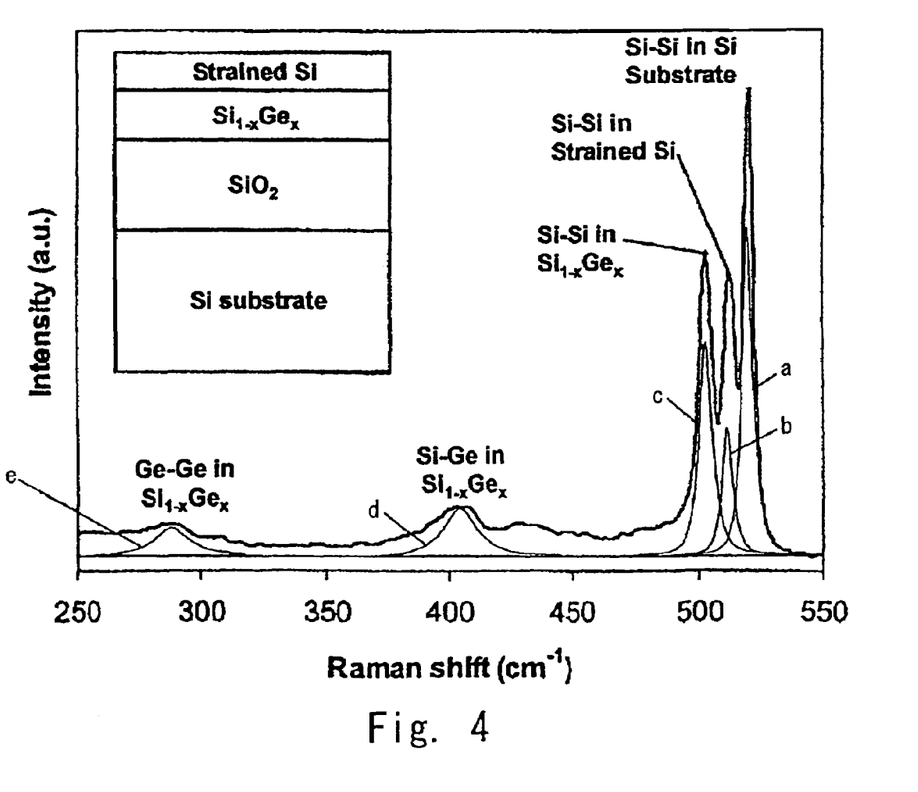
FIG. 4 is a diagram illustrating a relationship between a wavelength and a spectral intensity in each layer obtained when the Raman spectrum of the semiconductor material is measured.

When the excitation light capable of reaching the single crystal silicon substrate 3A of the wafer 3 is selectively used, the Raman spectra of the respective layers 3A-3D constituting the wafer 3 can be obtained as shown in FIG. 4. The Raman spectra can confirm the following:

a. Si—Si band of single crystal silicon substrate 3A
  b. Si—Si band of srained silicon layer 3D
  c. Si—Si band of SiGe layer 3C
  d. Si—Ge band of SiGe layer 3C
  e. Ge—Ge band of SiGe layer 3C The Gaussian function, Lorenz function or a function of a linear sum of the Gaussian and Lorenz types is fitted to the spectra so that a shift $v_1$, a full width at half maximum $\omega_1$, intensity $I_1$, or area S i (i=a, b, c, d, e) of each band is obtained. The function to be fitted can be optionally selected and set depending on a shape of each spectrum. When a large variation is generated in the optical system, gas laser may be used as the excitation light for plasma line correction to correct the variation by means of the plasma line.

A stress $\sigma_1$ of the strained silicon layer 3D and a stress $\sigma_2$ of the SiGe layer 3C are calculated from the band shift $v_i$ (i=a, b, c, d, e) of the foregoing parameters in the following procedure.

1. Correction values $\Delta\phi_{cv}$, $\Delta\phi_{dv}$ and $\Delta\phi_{ev}$ of the band shifts in the respective layers are calculated in response to a difference $\Delta\phi_{bv}$ between a Si—Si band shift $v_a$ of the single crystal silicon substrate 3A (band shift in non-stress state) and a Si—Si band shift $V_b$ of the strained silicon layer 3D and a temperature estimated by the Si—Si band shift $v_a$ of the single crystal silicon substrate 3A.

2. The stress $\sigma_1$ of the strained silicon layer 3D is calculated from the band shift difference $\Delta\phi_{bv}$ calculated in 1, and the stress $\sigma_2$ of the SiGe layer 3C is calculated from the correction values $\Delta\phi_{cv}$, $\Delta\phi_{dv}$ and $\Delta\phi_{ev}$ of the band shifts in the respective layers calculated in 1. The stress $\sigma_2$ of the SiGe layer 3C is calculated through the creation of a calibration curve using one, two or all of the three band shifts as parameters.

Examples of the calibration curve are as follows:

$$\delta_1 = p_1 \times \Delta\phi bv$$

$$\delta_2 = p_2 \times \Delta\phi cv + p_2 \times \Delta\phi_{dv} + p_3 \times \Delta\phi_{ev} + p_4$$

In the foregoing formulas, p1, p2, p3 and p4 are constants. Further, it is possible to calculate the stress $\sigma_1$ of the strained silicon layer 3D and the stress $\sigma2$ of the SiGe layer 3C by means of a multivariate analysis using all of the difference $\Delta\phi_{bv}$ and the correction values $\Delta\phi_{cv}$, $\Delta\phi_{dv}$ and $\Delta\phi_{ev}$ of the band shifts as the parameters.

As described, the current temperature of the semiconductor material 3 itself is estimated from the band (peak) shift amount of the Raman spectrum in the non-stress state from the monoscrystal silicon substrate 3A in the semiconductor material 3, and the band shift amounts of the Raman spectra in the strained silicon layer 3D and the SiGe layer 3C stacked on one another on the substrate 3A are corrected. In the foregoing manner, the stresses $\sigma_1$ and $\sigma_2$ of the strained silicon layer 3D and the SiGe layer 3C can be accurately measured irrespective of the generation of the peak shift of the Raman spectrum influenced by the temperature of the semiconductor substrate 3 itself due to the changing ambient temperature and the like. Accordingly, it is no longer necessary to provide a temperature adjusting mechanism for maintaining the temperature of the semiconductor material 3 itself at a constant degree and the additional steps such as measuring the Raman spectrum of the specimen for correcting the temperature, which is prepared apart from the semiconductor material, prior to the measurement of the semiconductor material 3 to be measured so as to correct the peak shift of the Raman spectrum influenced by the temperature change of the semiconductor material 3 based on the measurement information. As a result, the stress measurement can be realized with high accuracy, at a high speed and at a lower cost for eliminating any influence of the temperature.

In order to handle optical system fluctuations resulting from changes in ambient temperature, for example, wavelength deviation caused by slight distortion of optical parts, or positional shift of Raman spectral peak associated with temperature changes of semiconductor material itself to be measured, it is possible to take in a gas laser plasma line together with Raman light (scattering light associated with irradiation of excitation light), correct the peak position of Raman spectra using the peak positional shift of this plasma line, and measure the stress from the peak position of the corrected Raman spectra. In such event, add the atomic beam of emission lamp may be used in place of gas laser plasma line as reference light (for wavelength calibration).

Further, it is possible to calculate a film thickness t1 and a film thickness t2 of the strained silicon layer 3D and the SiGe layer 3C and a Ge content x in the SiGe layer 3C from the foregoing respective parameters $\phi_i$, $\omega_i$ and $I_i$ or $S_i$ (i=a, b, c, d, e) at the same time as the calculation of the stresses $\sigma_1$ and $\sigma_2$ of the strained silicon layer 3D and the SiGe layer 3C. The calculation procedure is as follows.

1. $\Delta\phi bv$ $\Delta\phi cv$ $\Delta\phi dv$ and $\Delta\phi ev$ are calculated in the same manner as in 1 described earlier.

2. The film thickness t1 and the film thickness t2 of the strained silicon layer 3D and the SiGe layer 3C and the Ge content x in the SiGe layer 3C can be calculated by means of the following operational expression.

$$\begin{bmatrix} \delta_1 \\ \delta_t \\ t_1 \\ t_2 \\ x \end{bmatrix} = \begin{bmatrix} p_{11} & p_{12} & p_{13} & p_{14} & p_{15} \\ \bullet & p_{22} & p_{23} & p_{24} & p_{25} \\ \bullet & \bullet & p_{33} & p_{34} & p_{35} \\ \bullet & \bullet & \bullet & p_{44} & p_{45} \\ \bullet & \bullet & \bullet & \bullet & p_{55} \end{bmatrix} \begin{bmatrix} b_1 \\ b_2 \\ b_3 \\ b_4 \\ b_5 \end{bmatrix}$$

In the foregoing formula, $p_{ij}$ (i=j=1-5) is a constant, and $b_1$, $b_2$, $b_3$, $b_4$ and $b_5$ respectively represent any of $\Delta\phi_{bv}$, $\Delta\phi_{cv}$, $\Delta\phi_{dv}$, $\Delta\phi_{ev}$, $\omega_i$, $I_i$ or $S_i$, or an intensity ratio or an area ratio, and the combinations thereof are optionally determined depending on the accuracy of the respective calculated values thereof.

The foregoing calibration curves (constants $p_i$ and $p_{ij}$ can be previously obtained by looking into the change of the respective parameters depending on the change of the stress, film thickness and Ge content.

Thus, the peak shift amount, spectral full width at half maximum, spectral intensity, spectral area and the like of each layer constituting the semiconductor material 3 are used as the parameters to implement the predetermined stress calculation and also to calculate the respective physical quantities such as the film thicknesses of the strained silicon layer 3D and the SiGe layer 3C and/or the Ge content in the SiGe layer 3C. Thereby, the quality control of the semiconductor material 3 can achieve a higher performance, which further improves the quality of the manufactured semiconductor device. Further, the inspecting steps and the inspecting facility can be simplified, possibly contributing to the productivity improvement and the reduction of the manufacturing cost. Note, the silicon germanium layer can be substituted by a $SiO_2$ layer as an alternative example.

Figure 5:
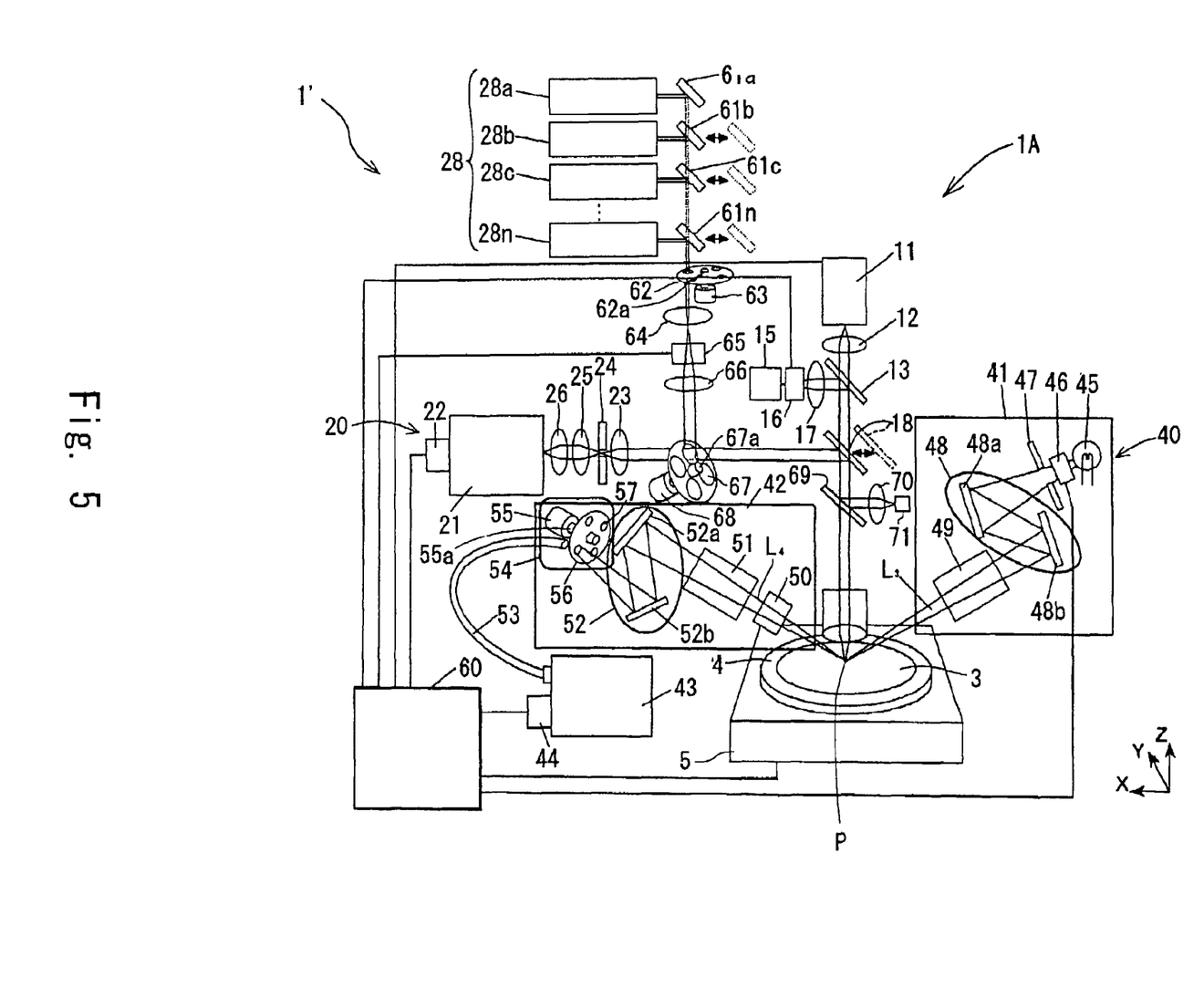
FIG. 5 is a view illustrating a constitution of a stress measuring system as a main part of a substrate inspection apparatus according to the second embodiment.
Figure 9:
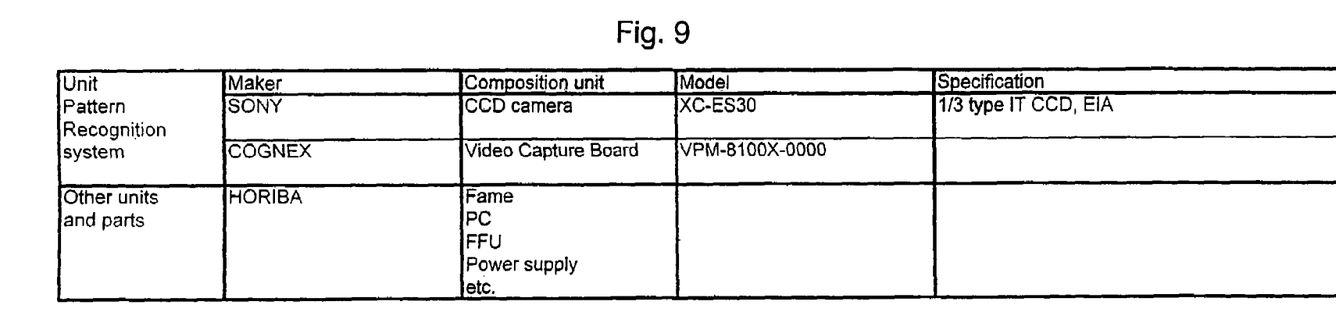
FIG. 9 is a supplemental equipment table for the second embodiment.

FIG. 5 illustrates a constitution of a stress measuring system 1A which is a main part of a substrate inspection apparatus 1' according to a second embodiment of the present invention. In the substrate inspection apparatus 1' according to the second embodiment shown in FIG. 1F and FIG. 7, an ellipsometer optical system 40 is installed as well as the Raman spectroscopic optical system 20. The ellipsometer optical system 40 comprises an incident optical system 41 for irradiating a multi-wavelength polarized light $L_3$ from an obliquely upward direction relative to a surface of the specimen table 4 on one side on the measurement point P of the wafer 3 disposed on the specimen table 4 with which the optical microscope 10 comes into focus, a detection optical system 42 provided in an obliquely upward direction relative to the surface of the specimen table 4 on another side, an spectrograph 43 and a detector 44. FIG. 9 is a supplemental equipment table for the second embodiment.

The incident optical system 41 comprises a white light source 45 formed from, for example, a xenon lamp for emitting a light having a wide wavelength region of, for example, 190-830 nm, a shutter 46, a slit 47 for condensing the light emitted from the white light source 45, a beam reducing optical system 48 and a polarized light polarizer 49. The beam reducing optical system 48 is formed from, for example, two concave mirrors 48a and 48b.

The detection optical system 42 serves to enter a polarized light $L_4$ reflected when the polarized light $L_3$ is irradiated on the measurement point P on the surface of the wafer 3 into the spectrograph 43 and comprises a phase modulating element 50, an analyzer 51, a beam reducing optical system 52 formed from two concave mirrors 52a and 52b and an optical fiber 53 for retrieving a signal to be transmitted to the spectrograph 43, wherein a pinhole part 54 is provided between the beam reducing optical system 52 and the optical fiber 53.

The pinhole part 54 is formed from a plurality of pinholes 57 having different sizes (diameter) spaced at appropriate intervals on a same circumference of a disk 56, for example, mounted on a rotation shaft 55a of a stepping motor 55. Therefore, as shown in FIG. 5, the light emitted from the beam reducing optical system 52 enters the optical fiber 53 via the pinhole 57 only when any of the pinholes 57 is positioned on an optical path connecting the beam reducing optical system 52 and the optical fiber 53.

The reflected light from the wafer 3 which entered the spectrograph 43 of the ellipsometer optical system 40 is checked for its intensity by the detector 44 per wavelength and fetched by the computer 60 as a spectrum. In the computer 60 is incorporated a control program Pa for calculating a film thickness or a refractivity at the measurement point P from spectrum data measured from the wafer 3 based on a relationship between spectrum and film thickness or a relationship between spectrum and refractivity which is previously stored therein.

The rest of the constitution of the substrate inspection apparatus 1' according to the second embodiment, that is the constitution of the Raman spectroscopic optical system 20 is the same as in the description recited in the first embodiment. Therefore, any like component is provided with the same reference symbol and is not described here again. By the way, for transmission of light from laser head to Raman optical system, optical fiber may be used.

In the substrate inspection apparatus 1' according to the second embodiment, not only the stresses $\sigma 1$ and $\sigma 2$ of the strained silicon layer 3D and the SiGe layer 3C can be measured by the Raman spectroscopic optical system 20, but also the film thickness and the refractivity can be highly accurately measured by the ellipsometer optical system 40. Thereby, when the semiconductor substrate using the strained silicon, which has been increasingly used in the manufacturing of the semiconductor device in recent years, is used as the measuring object, the respective physical quantities such as the internal stresses of the strained silicon layer 3D and the SiGe layer 3C which is the ground layer thereof and the Ge content in the SiGe layer 3C can be reliably measured so that the substrate can be highly accurately inspected.

However, because the present invention is aimed at measuring the stresses of the strained silicon layer 3D and the SiGe layer 3C which is the ground layer thereof in the semiconductor material (substrate) using the strained silicon, the problems included in the conventional technology can be fully solved by the constitution recited in the first embodiment in which the ellipsometer optical system 40 recited in the embodiment 2 is not provided. The ellipsometer may be a spectroscopic ellipsometer or single wavelength ellipsometer.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A method of measuring a stress of a semiconductor material by irradiating an excitation light on a semiconductor material formed from providing a silicon germanium layer and a strained silicon layer in a multilayer structure on a single crystal silicon substrate from the direction of the strained silicon layer, and measuring an internal stress of the semiconductor material from peak position information of a Raman spectrum of scattered light from an irradiating point, comprising:

providing a light having a wavelength capable of reaching the single crystal silicon substrate as the excitation light;
   collecting the excitation light from the semiconductor material;
   estimating a temperature of the semiconductor material from a shift amount of the peak position of the Raman spectrum of the scattered light from the substrate in accordance with the irradiation of the excitation light of the foregoing wavelength;
   correcting shift amounts of the peak positions of the Raman spectra in the strained silicon layer and in the silicon germanium layer with the estimated temperature; and
   calculating the internal stresses of the strained silicon layer and the silicon germanium layer from the corrected peak position information of the Raman spectra in the respective layers.

2. The method of measuring the stress of the semiconductor material according to claim 1, and further comprising that at least one of the shift amount of the peak position, spectral full width at half maximum, spectral intensity and spectral area of the Raman spectrum in each of the single crystal silicon substrate, strained silicon layer and silicon germanium layer constituting the semiconductor material are used as parameters to calculate film thicknesses of the strained silicon layer and the silicon germanium layer and/or a germanium content in the silicon germanium layer at the same time as the calculation of the internal stresses.

3. A device for measuring a stress of a semiconductor material, wherein an excitation light unit irradiates light on a semiconductor material, formed from providing a silicon germanium layer and a strained silicon layer in a multilayer structure on a single crystal silicon substrate, from the direction of the strained silicon layer, and an internal stress of the semiconductor material is measured from peak position information of the Raman spectrum of a scattered light from the irradiating point, the device comprising;

a laser source for generating the excitation light having a wavelength capable of reaching the single crystal silicon substrate;
   a Raman spectroscopic optical system for irradiating the excitation light onto the semiconductor material at a measurement point from the strained-silicon-layer side to the single crystal silicon substrate, receiving the excitation light from the semiconductor material from the strained-silicon layer side to the single crystal silicon substrate and outputting peak position shift information of the Raman spectrum of the scattered light from the measurement point on which the excitation light is irradiated; and
   an operating unit for estimating a temperature of the semiconductor material from the peak position shift information of the Raman spectrum, correcting the peak position shift amounts of the Raman spectra in the strained silicon layer and in the silicon germanium layer using the estimated temperature and calculating the internal stresses of the strained silicon layer and the silicon germanium layer from the corrected peak position information of the Raman spectra in the respective layers.

4. The device for measuring the stress of the semiconductor material according to claim 3, and further comprising that the operating unit is provided with a means for calculating the film thicknesses of the strained silicon layer and the silicon germanium layer and/or the germanium content in the silicon germanium layer at the same time as the calculation of the internal stresses using at least one of the shift amount of the peak position, spectral full width at half maximum, spectral intensity and spectral area of the Raman spectrum in each of the single crystal silicon substrate, strained silicon layer and silicon germanium layer constituting the semiconductor material as parameters.

5. The device for measuring the stress of the semiconductor material according to claim 3, and further comprising the laser source includes a plurality of lasers having different wavelengths and that the Raman spectroscopic optical system is provided with a laser beam selecting means for selectively switching between the plurality of lasers having different wavelengths.

6. The device for measuring the stress of the semiconductor material according to claim 4, and further comprising the laser source includes a plurality of lasers having different wavelengths and that the Raman spectroscopic optical system is provided with a laser beam selecting means for selectively switching between the plurality of lasers having different wavelengths.

7. In a device for measuring stress in a semiconductor material format with a silicon germanium layer and a strained silicon layer in a multi-layer structure on a single crystal silicon substrate, the improvement comprising;

an irradiating unit for irradiating wavelengths of light that penetrate the silicon germanium layer, strained silicon layer and substrate;
   a collecting unit for collecting Raman spectra from the silicon germanium layer, strained silicon layer and substrate;
   means for correcting temperature effects on the measured internal stress by estimating temperature from a shift amount of the peak position of a Raman spectra of scattered light from the substrate; and
   an operating unit for measuring the internal stress from peak position information of the Raman spectra in the silicon germanium layer and the strained silicon layer as corrected for temperature effects.

8. The device for measuring the stress in the semiconductor material according to claim 7, and further comprising in the operating unit, calculating the film thicknesses of the strained silicon layer and the silicon germanium layer and/or the germanium content in the silicon germanium layer at the same time as the calculation of the internal stresses using at least one of the shift amount of the peak position, spectral full width at half maximum, spectral intensity and spectral area of the Raman spectrum in each of the single crystal silicon substrate, strained silicon layer and silicon germanium layer constituting the semiconductor material as parameters.

9. The device for measuring the stress in the semiconductor material according to claim 7, and further comprising a Raman spectroscopic optical system that is provided with a laser beam unit for selectively switching between a plurality of laser sources having different wavelengths to select the appropriate wavelengths for penetration.

10. A method of measuring a stress of a semiconductor material by irradiating an excitation light on a semiconductor material formed from providing a silicon dioxide layer and a strained silicon layer in a multilayer structure on a single crystal silicon substrate from the direction of the strained silicon layer, and measuring an internal stress of the semiconductor material from peak position information of a Raman spectrum of scattered light from an irradiating point, comprising:

providing a light having a wavelength capable of reaching the single crystal silicon substrate as the excitation light;

collecting the excitation light from the semiconductor material;

estimating a temperature of the semiconductor material from a shift amount of the peak position of the Raman spectrum of the scattered light from the substrate in accordance with the irradiation of the excitation light of the foregoing wavelength, shift amounts of the peak positions of the Raman spectra in the strained silicon layer and in the silicon dioxide layer are corrected with the estimated temperature; and calculating the internal stresses of the strained silicon layer and the silicon dioxide layer from the corrected peak position information of the Raman spectra in the respective layers.

11. The method of measuring the stress of the semiconductor material according to claim 10, and further comprising that at least one of the shift amount of the peak position, spectral full width at half maximum, spectral intensity and spectral area of the Raman spectrum in each of the single crystal silicon substrate, strained silicon layer and silicon dioxide layer constituting the semiconductor material are used as parameters to calculate film thicknesses of the strained silicon layer and the silicon dioxide layer at the same time as the calculation of the internal stresses.

12. The device of claim 5 wherein the laser source includes an Ar ion laser and a He—Cd ion laser.

13. The device of claim 3 further including an ellipsometric optical system to measure properties of the semiconductor material.

14. The device of claim 3 further including an optical microscope for aligning an optical axis with the measurement point on the semiconductor material and a movable mirror for positioning the optical axis in alignment with the Raman spectroscope optical system.

15. The device of claim 14 wherein the laser source includes a plurality of lasers of different wavelengths from 325 nm to 514 nm.

16. The device of claim 3 further including means for detecting a focal point of a laser source wavelength and relatively adjusting the measurement point on the semiconductor material to the focal point.

17. The device of claim 3 further including a robot unit and a specimen table, the robot unit selects a specimen of semiconductor material and positions the specimen on the specimen table for alignment with the Raman spectroscope optical system.

18. The device of claim 13 where the operating unit further calculates film thickness of the strained silicon layer and the silicon germanium layer.

19. The device of claim 18 where the operating unit further calculates the Ge content in the silicon germanium layer when calculating the internal stresses of the strained silicon layer and silicon germanium layer.

20. The device of claim 3 further including a source of a multi-wavelength polarized light directed onto the measurement point and an ellipsometer optical system for providing measurements of the multi-wavelength polarized light from the measurement point to the operating unit for calculating film thickness and refractivity at the measurement point.

* * * * *